US012071651B2

(12) United States Patent
Tsao et al.

(10) Patent No.: US 12,071,651 B2
(45) Date of Patent: Aug. 27, 2024

(54) DILUTION TAGGING FOR QUANTIFICATION OF BIOLOGICAL TARGETS

(71) Applicant: BillionToOne, Inc., Menlo Park, CA (US)

(72) Inventors: David Tsao, Menlo Park, CA (US); Patrick Ye, Menlo Park, CA (US); Sukrit Silas, Menlo Park, CA (US); Oguzhan Atay, Menlo Park, CA (US)

(73) Assignee: BillionToOne, Inc., Menlo Park, CA (US)

( * ) Notice: Subject to any disclaimer, the term of this patent is extended or adjusted under 35 U.S.C. 154(b) by 591 days.

(21) Appl. No.: 16/533,444

(22) Filed: Aug. 6, 2019

(65) Prior Publication Data

US 2020/0040380 A1   Feb. 6, 2020

Related U.S. Application Data

(60) Provisional application No. 62/715,175, filed on Aug. 6, 2018.

(51) Int. Cl.
*C12Q 1/6816* (2018.01)
*C12Q 1/6806* (2018.01)
*C12Q 1/6851* (2018.01)
*C12Q 1/6853* (2018.01)
*C12Q 1/6876* (2018.01)
*G16B 40/10* (2019.01)

(52) U.S. Cl.
CPC ......... *C12Q 1/6816* (2013.01); *C12Q 1/6806* (2013.01); *C12Q 1/6851* (2013.01); *C12Q 1/6853* (2013.01); *C12Q 1/6876* (2013.01); *G16B 40/10* (2019.02); *C12Q 2525/161* (2013.01); *C12Q 2525/179* (2013.01); *C12Q 2537/143* (2013.01); *C12Q 2545/114* (2013.01); *C12Q 2600/166* (2013.01)

(58) Field of Classification Search
CPC .. C12Q 1/6806; C12Q 1/6851; C12Q 1/6853; C12Q 2525/161; C12Q 2525/179; C12Q 2537/143; C12Q 2545/114; C12Q 2531/113; C12Q 2535/122; C12Q 2563/179
See application file for complete search history.

(56) References Cited

U.S. PATENT DOCUMENTS

| 5,846,719 | A  | 12/1998 | Brenner et al. |
| 6,013,445 | A  | 1/2000  | Albrecht et al. |
| 8,105,422 | B2 | 1/2012  | Betting et al. |
| 8,195,415 | B2 | 6/2012  | Fan et al. |
| 8,467,976 | B2 | 6/2013  | Lo et al. |
| 8,688,388 | B2 | 4/2014  | Dzakula et al. |
| 8,877,442 | B2 | 11/2014 | Quake et al. |
| 9,512,480 | B2 | 12/2016 | Lo et al. |
| 9,944,973 | B2 | 4/2018  | Willey et al. |
| 2007/0009884 | A1 | 1/2007  | Stoughton et al. |
| 2007/0092869 | A1 | 4/2007  | Fulmer-Smentek et al. |
| 2008/0124712 | A1 | 5/2008  | Hantash et al. |
| 2008/0274458 | A1 | 11/2008 | Latham et al. |
| 2010/0323352 | A1 | 12/2010 | Lo et al. |
| 2011/0033861 | A1 | 2/2011  | Wu et al. |
| 2011/0201507 | A1 | 8/2011  | Rava et al. |
| 2012/0021919 | A1 | 1/2012  | Scholl et al. |
| 2012/0270739 | A1 | 10/2012 | Rava et al. |
| 2013/0022973 | A1 | 1/2013  | Hansen et al. |
| 2013/0103320 | A1 | 4/2013  | Dzakula et al. |
| 2013/0130923 | A1 | 5/2013  | Ehrich et al. |
| 2014/0195164 | A1 | 7/2014  | Lo et al. |
| 2015/0099266 | A1 | 4/2015  | Samuels et al. |
| 2015/0133391 | A1 | 5/2015  | De Vlaminick et al. |
| 2015/0152474 | A1 | 6/2015  | Pawlowski et al. |
| 2015/0284783 | A1 | 10/2015 | Canton |
| 2016/0040229 | A1 | 2/2016  | Talasaz et al. |
| 2016/0130649 | A1 | 5/2016  | Xie et al. |

(Continued)

FOREIGN PATENT DOCUMENTS

WO    2011091046 A1    7/2011
WO    2011156795 A2    12/2011

(Continued)

OTHER PUBLICATIONS

Herter-Sprie et al. Activating mutations in ERBB2 and their impact on diagnostics and treatment. Frontiers in Oncology 2013; 3: 86; doi: 10.3389/fonc.2013.00086 (Year: 2013).*
China National Intellectual Property Administration, Office Action, CN Patent Application No. 201980065828.6, Sep. 17, 2021, 11 pages.
International Search Report and the Written Opinion, Application No. PCT/US19/45331, mailed Oct. 25, 2019.
Tsao, et al. "A novel high-throughput molecular counting method with single base-pair resolution enables accurate single-gene NIPT," bioRxiv, Apr. 3, 2019 (Apr. 3, 2019), pp. 1-20.
International Preliminary Report on Patentability for PCT/US18/45434, mailed Jul. 14, 2020.
Applied Biosystems, Application Note: Detection and Quantification of Sequence Variants from Sanger Sequencing 1 Traces, Determination of minor alleles by analyzing peak height dat, Retrieved from the internet :< URL: http://www.nstillcase.com/Downloads/seq-quantification-app-note.pdf>, copyright = 2013.

(Continued)

*Primary Examiner* — Angela M. Bertagna
(74) *Attorney, Agent, or Firm* — Fenwick & West LLP

(57) ABSTRACT

Embodiments of a method for accurate determination of biological target abundance can include generating a first set of molecules associated with a target sequence, where the first set of molecules includes a first set of dilution tags associated with a relative concentration profile; generating a second set of molecules including a second set of dilution tags associated with the first set of dilution tags; generating a dilution tagged mixture; amplifying the subsets of dilution tagged genetic targets using the second set of molecules; generating a modified dilution tagged mixture from the amplified subsets; determining, for the biological sample, a count of the distinct molecules including the target sequence; and/or determining, for the biological sample, an assessment of relative concentrations distinct species, such as over a vast dynamic range.

20 Claims, 10 Drawing Sheets

(56) References Cited

U.S. PATENT DOCUMENTS

| | | | |
|---|---|---|---|
| 2016/0168564 | A1 | 6/2016 | Jacobson et al. |
| 2016/0222391 | A1 | 8/2016 | Krieg et al. |
| 2016/0251719 | A1 | 9/2016 | Umbarger |
| 2016/0319345 | A1 | 11/2016 | Gnerre et al. |
| 2017/0175187 | A1 | 6/2017 | Rabinowitz et al. |
| 2017/0275691 | A1 | 9/2017 | Karius et al. |
| 2017/0327869 | A1 | 11/2017 | Schutz et al. |
| 2018/0010176 | A1 | 1/2018 | Patel |
| 2018/0023125 | A1 | 1/2018 | Talasaz et al. |
| 2018/0127804 | A1 | 5/2018 | Dean et al. |

FOREIGN PATENT DOCUMENTS

| | | | | |
|---|---|---|---|---|
| WO | 2012058316 | A1 | | 5/2012 |
| WO | 2012129363 | A1 | | 9/2012 |
| WO | 2014039556 | A1 | | 3/2014 |
| WO | 2014082032 | A1 | | 5/2014 |
| WO | 2017165864 | A1 | | 9/2017 |
| WO | 2017210372 | A1 | | 12/2017 |
| WO | 2018031486 | A1 | | 2/2018 |
| WO | 2014127484 | A1 | | 11/2018 |
| WO | WO-2019200341 | A1 | * | 10/2019 ........... C12Q 1/6813 |

OTHER PUBLICATIONS

Carr, I. M., et al., "Inferring relative proportions of DNA variants from sequencing electropherograms", Bioinformatics, vol. 25, Issue 24, hllps://doi.org/10.1093/bioinformatics/btp583,1 0/09/2009, 3244-3250.

Curci, Pasquale Luca, et al., "How a Small Double-Stranded Trick Can Mislead Sanger Sequencing", J Biomol Tech. vol. 26, Issue 3, Sep. 1, 2015, 80-82.

International Search Report and the Written Opinion of the International Searching Authority, Application No. PCT/US18/45419, dated Dec. 21, 2018.

International Search Report and Written Opinion for PCT Application No. PCT/US2018/045394 mailed Oct. 10, 2018.

International Search Report and the Written Opinion, Application No. PCT/US19/014340, mailed Mar. 29, 2019.

Kaboev, 0. K., et al., "PCR hot start using primers with the structure of molecular beacons {hairpin-like structure)", Nucl Acids Res, Sep. 12, 2000, vol. 28, No. 21.

Lun, Fiona M.F., et al., "Noninvasive prenatal diagnosis of monogenic diseases by digital size selection and relative mutation dosage on DNA in maternal plasma.", PNAS vol. 105, Dec. 16, 2008, 19920-19925.

Quail, M.A., et al., "SAS I-Seq: sample assurance Spike-Ins, and highly differentiating 384 barcoding for Illumina sequencing.", BMC Genomics, 2014, 1-12.

Silas, S., et al., "Direct CRISPR spacer acquisition from RNA by a natural reverse transcriptase-Cas1 fusion protein.", Science, Feb. 26, 2016, 1-31.

Sinha, R., et al., "Index Switching Causes "Spreading-Of-Signal" Among Multiplexed Samples In Illumina HiSeq 400(DNA Sequencing.", Apr. 9, 2017, 1-29.

Tourlousse, Dieter M., et al., "Synthetic spike-in standards for high-throughput 16S rRNA gene amplicon 4 sequencing", Biomedical Research Institute, National Institute of Advanced Industrial Science and Technology, Dec. 15, 2016.

Yan, Ti-Zhen, et al., "Reliable Detection of Paternal SNPs within Deletion Breakpoints for Non-Invasive Prenatal 2 Exclusion of Homozygous a-Thalassemia in Meternal Plasma", PLOS One, Sep. 29, 2011, vol. 6, No. 9, e24779, pp. 1-9.

International Search Report and Written Opinion for PCT Application No. PCT/US2018/045434 mailed Nov. 29, 2018.

International Preliminary Report on Patentability for PCT/US2018/045394, mailed Feb. 4, 2020.

International Preliminary Report on Patentability for PCT/US2018/045419 mailed Feb. 4, 2020.

China National Intellectual Property Administration, Second Office Action, Chinese Patent Application No. 201980065828.6, Apr. 13, 2022, 13 pages.

European Patent Office, Extended European Search Report, European Patent Application No. 19846980.1, Mar. 25, 2022, six pages.

\* cited by examiner

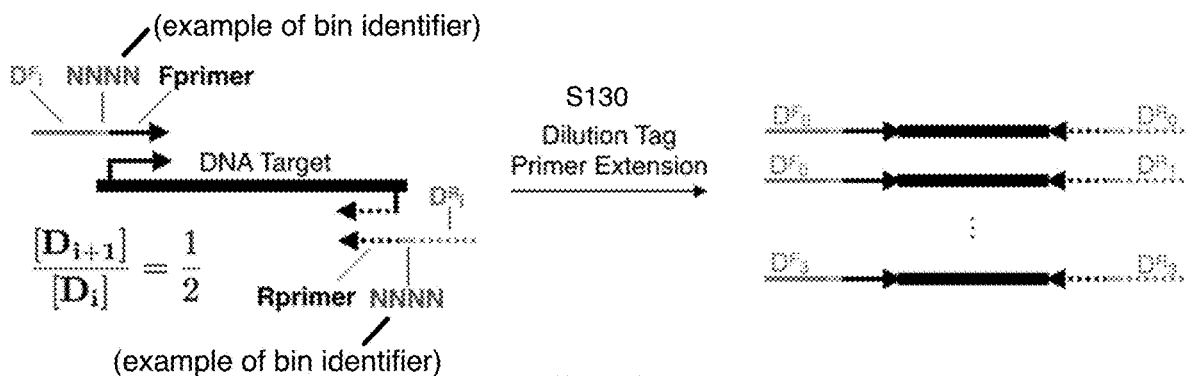
FIG. 4A
FIG. 4B
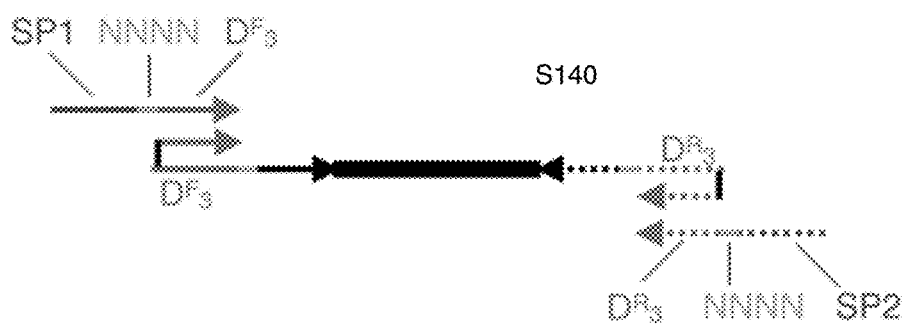
FIG. 4C

Generating a first set of molecules comprising different subsets of molecules comprising different dilution tags associated with the different subset of molecules, wherein the different dilution tags are associated with a relative concentration profile indicating different relative concentrations associated with the different dilution tags
S810

↓

Generating based on the first set of molecule and the cfDNA, a dilution tagged mixture comprising different subsets of dilution tagged genetic targets comprising the different dilution tags associated with the different relative concentrations indicated by the relative concentration profile
S820

↓

Generating a modified dilution tagged mixture comprising the different subset of dilution tagged genetic targets at modified concentrations based on the relative concentration profile
S830

↓

Determining an abundance of the biological target based on the modified dilution tagged mixture and the relative concentration profile
S840

FIG. 8

DILUTION TAGGING FOR QUANTIFICATION OF BIOLOGICAL TARGETS

CROSS-REFERENCE TO RELATED APPLICATIONS

This application claims the benefit of U.S. Provisional Application Ser. No. 62/715,175, filed on 6 Aug. 2018, which is incorporated herein in its entirety by this reference.

TECHNICAL FIELD

This disclosure relates generally to the field of diagnostics and therapeutics, and more specifically to a new and useful method and system for accurately quantifying the abundances of biological targets.

BRIEF DESCRIPTION OF THE FIGURES

FIGS. 4A-4C includes schematic representations of a variation of dilution tagging and determining target count;

FIG. 5A includes a specific example of theoretical calculations for the probability of detecting the presence of dilution tags given a number of target molecules. Six dilution tags (A-F) were assumed to be at consecutively decreasing concentrations by an order of magnitude. A Poissonian process was used (e.g., based on target molecules being more likely to attach to dilution tags of higher concentrations; etc.) to calculate the probability that at least one target molecule will attach to each dilution tag, resulting in detection of the dilution tag's presence via sequencing. As the number of target molecules increases, the probability of presence for each dilution tag increases until a number of target molecules are present that the probability of presence saturates.

FIG. 5B illustrates a specific heat map example of percentage of dilution tag bins with detected reads. Six dilution tags (A-F) at concentrations varying by orders of magnitude were added to DNA samples, each containing varying amounts of target molecules. Each dilution tag is associated with a bin identifier (e.g., where each oligonucleotide includes a dilution tag and a bin identifier, etc.) including a random four-nucleotide long sequence, where the bin identifiers allow for 256 bins. At $6*10^9$ target molecules, reads including all 256 bins were detected for all six dilution tags, indicating complete saturation of the target molecules by the dilution tags. Starting at $6*10^7$ target molecules, the lowest concentration dilution tag did not have detected reads in all bins. As the number of target molecules decreases, the percentage of bins with detected reads for the same concentration dilution tags continues to decrease. Dilution tags were removed after the initial PCR tailing reaction via column purification.

FIG. 5C includes a specific example of combining results in FIG. 5B with the theoretical probabilities in FIG. 5A to estimate the number of target molecules that were initially present. FIG. 5C illustrates the estimated number of target molecules as a function of experimental number of target molecules. The measured percentage of dilution tag bins with detected reads (as shown in FIG. 5B) was used to estimate the number of target molecules by best matching the theoretical probability of dilution tag presence (as shown in FIG. 5A). The experimental number of target molecules accounts for dividing the sample into six equal parts for separate amplification of each dilution tag, and for an estimated efficiency factor of 11.4%.

In FIG. 6A, DTag Eq displays strong convergence characteristics up to N=64000. In FIG. 6B, DTag Eq resolves<1.4 fold concentration difference between loci; where DTag Eq estimator is invariant to sampling depth and resilient to enrichment biases;

FIG. 8 includes a flowchart representation of a variation of an embodiment of a method for determining biological target abundance.

DESCRIPTION OF THE EMBODIMENTS

The following description of the embodiments (e.g., including variations of embodiments, examples of embodiments, specific examples of embodiments, other suitable variants, etc.) is not intended to be limited to these embodiments, but rather to enable any person skilled in the art to make and use.

1. Overview

Figure 1:
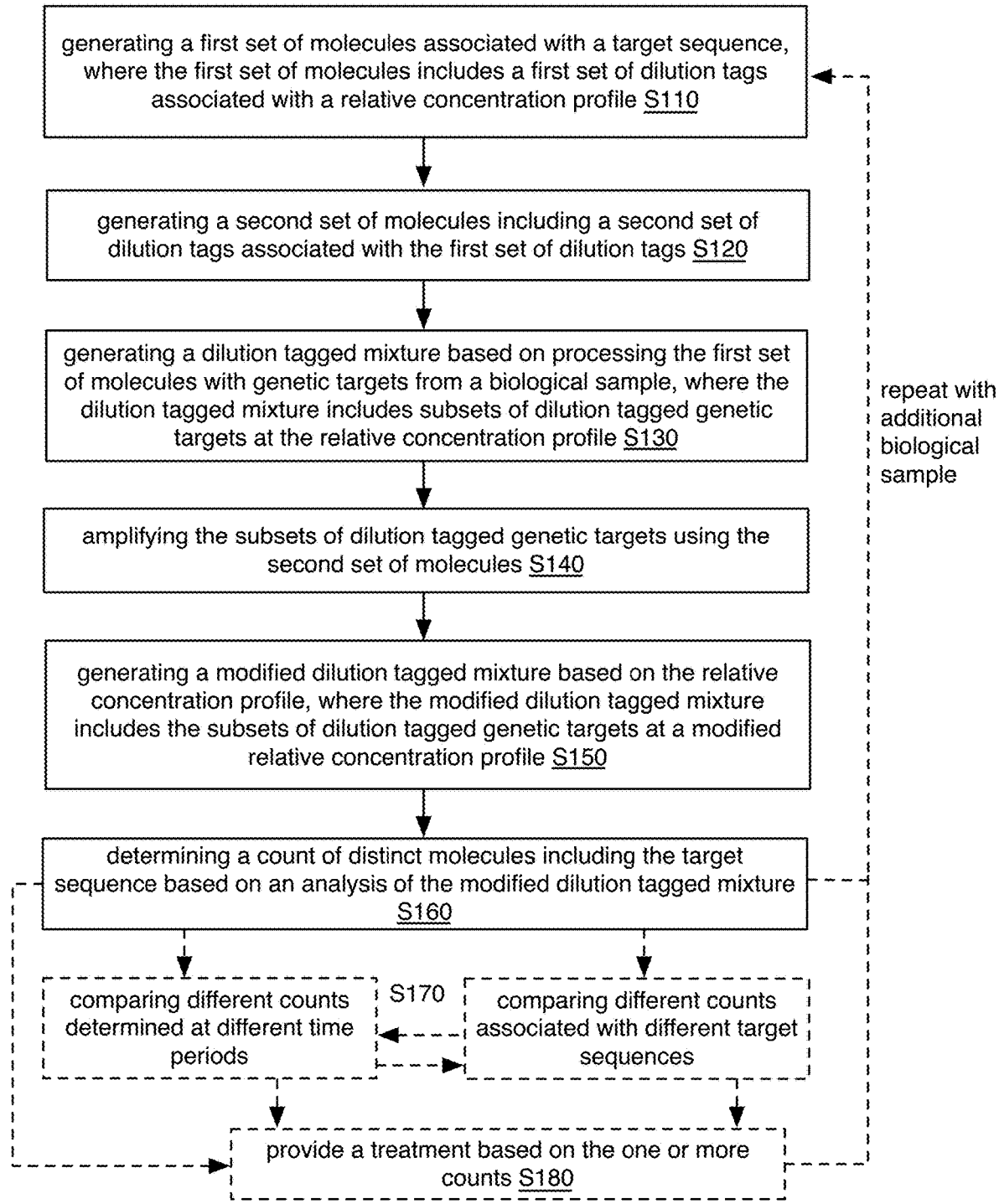
FIG. 1 includes a flowchart representation of a variation of an embodiment of a method for determining biological target abundance.
Figure 2:
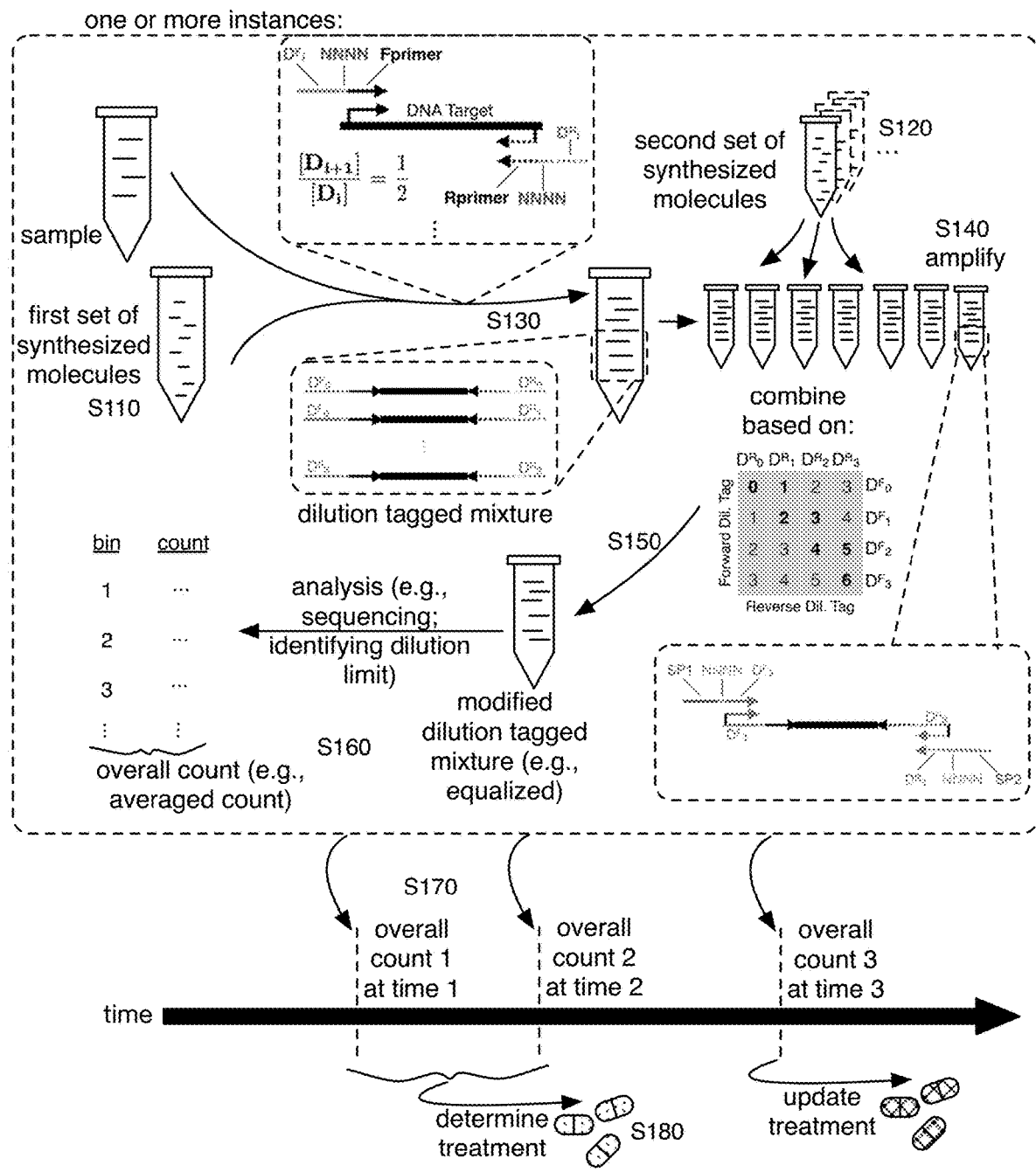
FIG. 2 includes a schematic representation of a variation of an embodiment of a method for determining biological target abundance.

As shown in FIGS. 1-2, embodiments of a method 100 for accurate determination of biological target abundance can include: generating a first set of molecules associated with a target sequence S110, where the first set of molecules includes a first set of dilution tags associated with a relative concentration profile; generating a second set of molecules including a second set of dilution tags associated with the first set of dilution tags S120; generating a dilution tagged mixture S130 based on processing the first set of molecules with genetic targets from a biological sample (e.g., blood sample), where the dilution tagged mixture includes subsets of dilution tagged genetic targets at the relative concentration profile; amplifying the subsets of dilution tagged genetic targets using the second set of molecules S140; generating a modified dilution tagged mixture from the amplified subsets of dilution tagged genetic targets based on the relative concentration profile S150, where the modified dilution tagged mixture includes the subsets of dilution tagged genetic targets at a modified relative concentration profile enabling reduction in a number of sequence reads (e.g., and associated sequencing cost, etc.) required to count the number of distinct molecules (e.g., through enabling logarithmic-based counting, such as logarithmic counting, Log Log counting, Hyper Log Log counting, etc.) including the target sequence; determining, for the biological sample, a count of the distinct molecules (e.g., DNA molecules) S160 including the target sequence based on an analysis of the modified dilution tagged mixture (e.g., based on a limiting dilution identified by the analysis); and/or determining, for the biological sample, an assessment of relative concentrations S170 of several distinct species (e.g., DNA or RNA molecules) including multiple target sequences that may be present at vastly differing abundances, i.e., over a vast dynamic range.

Embodiments of the method 100 can additionally or alternatively include: quantitatively comparing different counts S170 (e.g., counts determined at different time periods, such as through repeating portions of the method 100 for different biological samples collected at different time periods; counts associated with different target sequences; etc.); providing a treatment S180 based on the count; and/or any other suitable process.

In a specific example, as shown in FIG. 2, the method 100 can include: generating a first set of oligonucleotides including different subsets of oligonucleotides, where each subset of oligonucleotides includes oligonucleotides with a dilution tag unique to the subset of oligonucleotides (e.g., where the dilution tag is associated with a relative concentration profile for a dilution tagged mixture), a bin identifier (e.g., a 4N, "NNNN", randomized nucleotide sequence enabling for example, $4^4$ bins, etc.) configured to improve accuracy of count determination during post-processing, and a forward or reverse primer complementary to a target sequence; generating a second set of oligonucleotides including oligonucleotides with forward or reverse primers complementary to sequences of the dilution tags for the first set of oligonucleotides; performing a labeling process (e.g., two rounds of polymerase chain reaction) with the first set of oligonucleotides and genetic targets from a biological sample, thereby generating a dilution tagged mixture including different subsets of dilution tagged genetic targets identified by different dilution tag pairs ($D_i^F$, $D_j^R$) (e.g., where each dilution tag pair includes a forward and a reverse dilution tag) at different relative concentrations indicated by the relative concentration profile; performing an amplification process (e.g., subsequent rounds of polymerase chain reaction) with the second set of oligonucleotides and the dilution tagged mixture (e.g., subsampling the dilution tagged mixture; for each different subset of dilution tagged genetic targets, amplifying the dilution tagged genetic targets using complementary primers of the second set of oligonucleotides); generating an equalized dilution tagged mixture including the different subsets of dilution tagged genetic targets at substantially equal concentrations (e.g., to facilitate logarithmic-based counting) based on the relative concentration profile associated with the dilution tag pairs; and determining a count of distinct molecules including the target sequence based on an analysis of the equalized dilution tagged mixture (e.g., sequencing the equalized dilution tagged mixture; identifying the dilution tag pair of greatest relative concentration while not being detected in the sequence reads, where the relative concentration associated with the identified tag pair is indicative of the count; etc.).

In a specific example, a method 100 for determination of abundance of a biological target from cell-free DNA (cfDNA) can include: generating a first set of oligonucleotides including different subsets of oligonucleotides, where each subset of the different subsets of oligonucleotides includes oligonucleotides including: a dilution tag (e.g., associated with the subset of the different subsets of oligonucleotides, where the dilution tag is associated with the relative concentration profile indicating different relative concentrations of different dilution tag combinations; etc.), and a target-associated region (e.g., primer region) complementary to a target sequence associated with the biological target; generating a second set of oligonucleotides including dilution tag-associated regions complementary to nucleotide sequences of the dilution tags of the first set of oligonucleotides; performing a labeling process with the first set of oligonucleotides and the cfDNA, thereby generating a dilution tagged mixture including different subsets of dilution tagged genetic targets identified by the different dilution tag combinations at different relative concentrations indicated by the relative concentration profile; performing an amplification process with the second set of oligonucleotides and the dilution tagged mixture; generating a modified dilution tagged mixture including the different subsets of dilution tagged genetic targets at modified concentrations (e.g., based on the relative concentration profile associated with the different dilution tag combinations; etc.); and/or determining an abundance of the biological target based on the modified dilution tagged mixture and the relative concentration profile associated with the different dilution tag combinations. In specific examples, embodiments of the method 100 can include isolating cfDNA from one or more samples for subsequent analysis (e.g., determination of abundance of target molecules; etc.).

Figure 7:
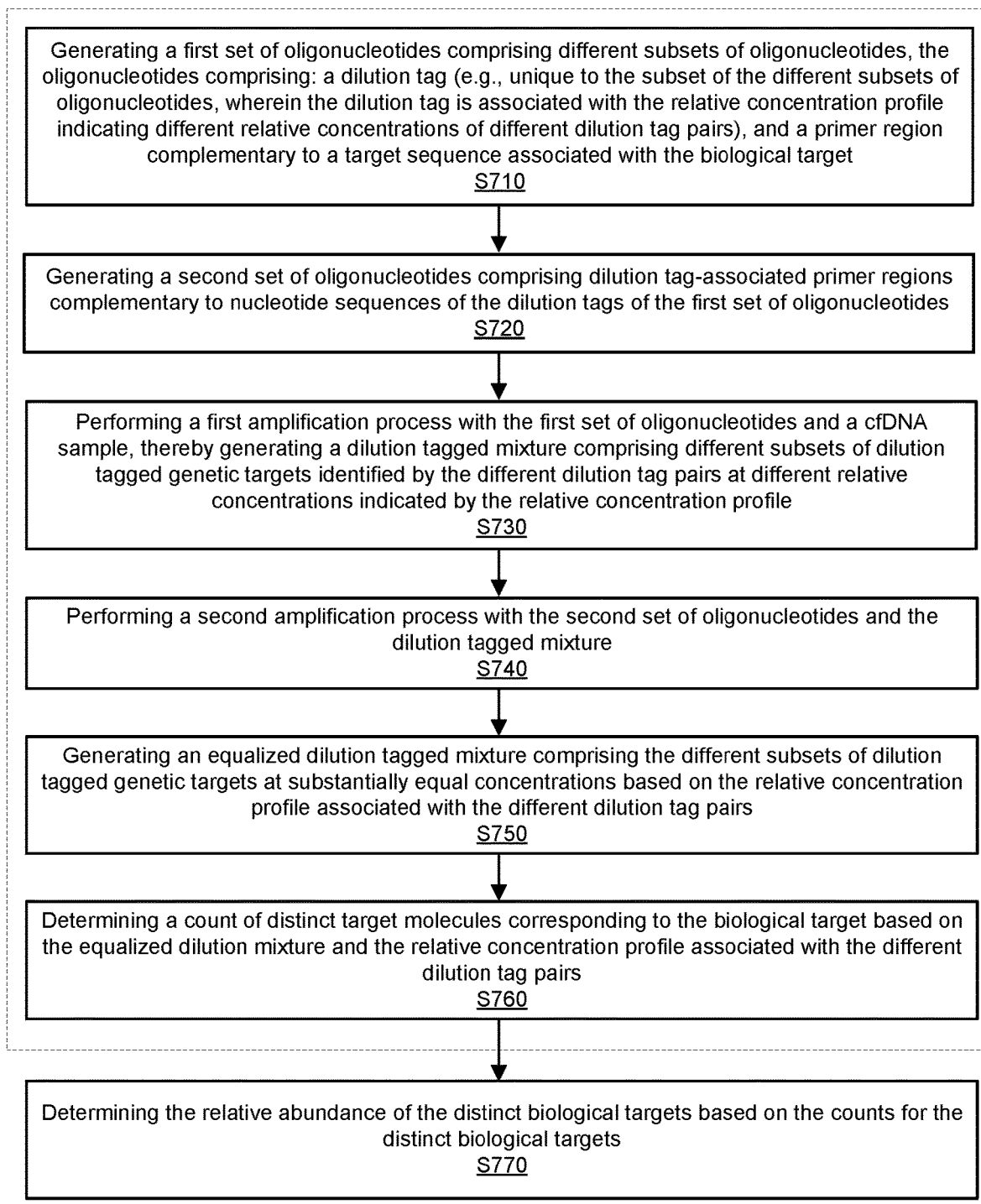
FIG. 7 includes a flowchart representation of a variation of an embodiment of a method for determining biological target abundance.

Embodiments of the method 100 and/or system 200 can be applied to determine relative abundance of distinct biological targets (e.g., over a high dynamic range), such as liquid biopsy, microbiome metagenomics, RNA-seq and/or any other suitable applications (e.g., applications requiring analysis of a relatively small number of sequence reads; applications requiring quantification for relative abundance of multiple loci at ratios of 1:1000 or lower; etc.). In examples (e.g., as shown in FIG. 7), a method 100 for accurate, high dynamic range determination of relative abundance of distinct biological targets from cell-free DNA (cfDNA) can include: for each biological target of the distinct biological targets associated with different genetic loci: generating S710 a first set of oligonucleotides including different subsets of oligonucleotides at predetermined relative concentrations based on a relative concentration profile, where each subset of the different subsets of oligonucleotides includes oligonucleotides including a dilution tag (e.g., unique to the subset of the different subsets of oligonucleotides, where the dilution tag is associated with the relative concentration profile indicating different relative concentrations of different dilution tag pairs; etc.), and a primer region complementary to a target sequence associated with the biological target; generating S720 a second set of oligonucleotides including dilution tag-associated primer regions complementary to nucleotide sequences of the dilution tags of the first set of oligonucleotides; performing S730 a labeling process with the first set of oligonucleotides and a cfDNA sample, thereby generating a dilution tagged mixture including different subsets of dilution tagged genetic targets identified by the different dilution tag pairs at different relative concentrations indicated by the relative concentration profile; performing S740 an amplification process with the second set of oligonucleotides and the dilution tagged mixture; generating S750 an equalized dilution tagged mixture including the different subsets of dilution tagged genetic targets at substantially equal concentrations based on the relative concentration profile associated with the different dilution tag pairs; and determining S760 a count of distinct target molecules corresponding to the biological target based on the equalized dilution tagged mixture and the relative concentration profile associated with the different dilution tag pairs; and/or determining S770 the relative abundance of the distinct biological targets based on the counts for the distinct biological targets.

In a specific example, the accurate, high dynamic range determination of the relative abundance of the distinct biological targets can be for liquid biopsy, where the distinct biological targets are associated with a cancer condition, and where determining the relative abundance of the distinct biological targets includes determining the relative abundance of the distinct biological targets for facilitating characterization of the cancer condition. In a specific example, the distinct biological targets include an ERBB2 gene (HER2) target, where determining the relative abundance of the distinct biological targets can include determining the relative abundance in relation to the ERBB2 gene target for facilitating characterization of the cancer condition (e.g., breast cancer condition) associated with the ERBB2 gene target. In a specific example, the distinct biological targets include a KRAS gene mutation, where determining the relative abundance of the distinct biological targets includes determining the relative abundance in relation to the KRAS gene mutation for facilitating characterization of the cancer condition associated with the KRAS gene mutation.

Any suitable portions of the embodiments of the method 100 and/or system 200 can be integrated in any suitable manner. In examples (e.g., as shown in FIG. 8), a method 100 for determination of abundance of a biological target from cell-free DNA (cfDNA) can include: generating S810 a first set of molecules including different subsets of molecules including different dilution tags associated with the different subsets of molecules, where the different dilution tags are associated with a relative concentration profile indicating different relative concentrations associated with the different dilution tags; generating S820, based on the first set of molecules and the cfDNA, a dilution tagged mixture including different subsets of dilution tagged genetic targets including the different dilution tags associated with the different relative concentrations indicated by the relative concentration profile; generating S830 a modified dilution tagged mixture including the different subsets of dilution tagged genetic targets at modified concentrations (e.g., based on the relative concentration profile; alternatively not based on the relative concentration profile; etc.); and/or determining S840 an abundance of the biological target based on the modified dilution tagged mixture and the relative concentration profile.

Figure 6A:
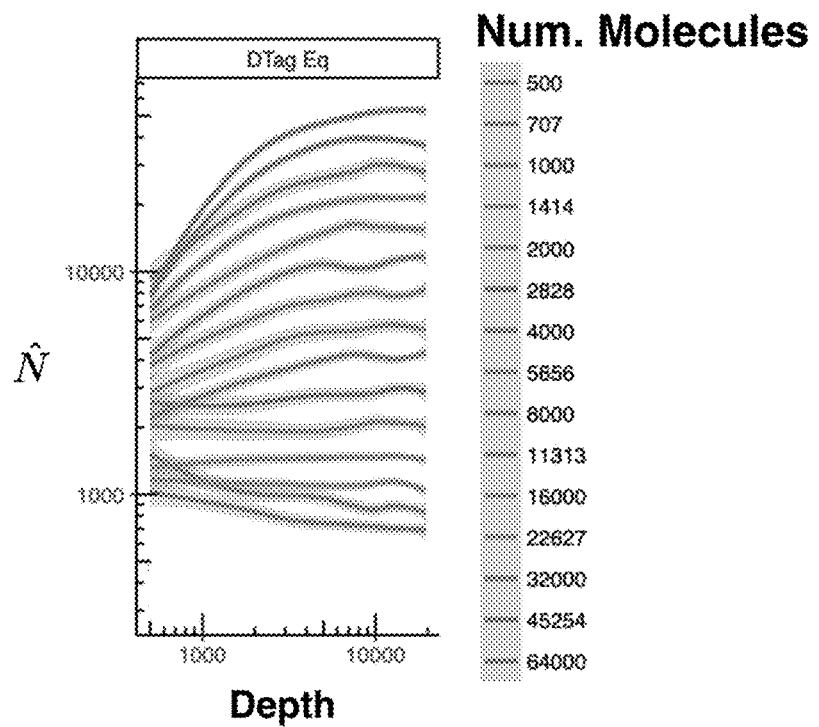
FIGS. 6A-6B include graph representations of Monte Carlo simulations at different sequencing depths for a variation of an embodiment of the method, such as for indicating that equalized dilution tagging can enable quantitative comparison of differentially enriched templates.
Figure 6B:
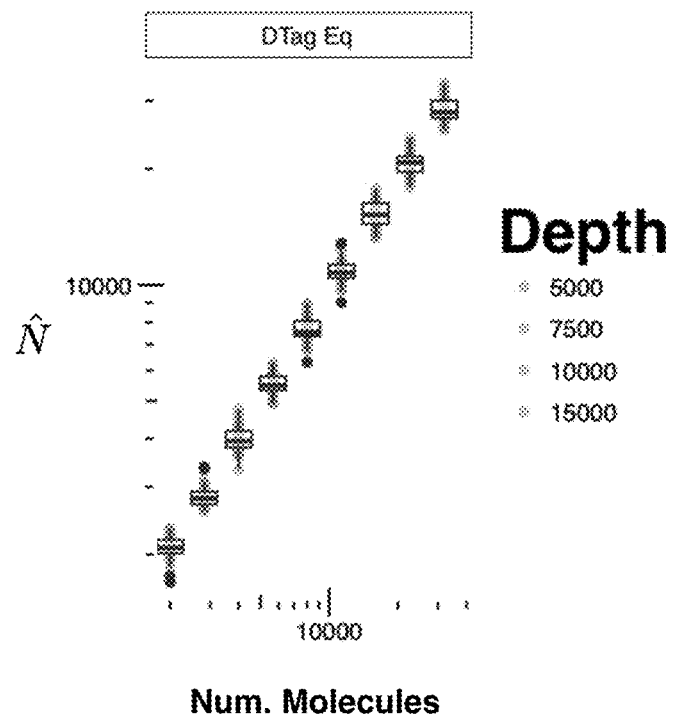

Embodiments of the method 100 and/or system 200 can function to enable logarithmic-based counting of distinct molecules (e.g., through leveraging insights associated with identifying the dilution tag pair corresponding to the limiting dilution at which the analyte falls below the detection threshold in the dilution series, etc.) possessing one or more target sequences, which can facilitate improvements in dynamic range (e.g., as shown in FIGS. 6A-6B; in relation to depth of sequencing required to accurately count, for example, rare target sequences, etc.), accuracy (e.g., by overcoming enrichment biases associated with conventional approaches, such as, but not limited to, GC bias and amplification noise, etc.), cost (e.g., through reducing the number of sequencing reads required for counting), deployability (e.g., through compatible integrations with next-generation sequencing systems; through compatible integrations with analysis systems associated with applications described herein, etc.), and/or other suitable aspects. In a specific example, any suitable portions of embodiments of the method 100 can be performed to accurately determine abundance of one or more target sequences, over a large dynamic range. Embodiments of the method 100 and/or system 200 can additionally or alternatively function to enable meaningful comparisons of counts determined at different times, for different target sequences (e.g., at different loci), for different biological samples (e.g., from different users; from different regions of the same user; etc.), and/or for any suitable differences in conditions. Embodiments of the method 100 and/or system 200 can be applied for quantification (e.g., abundance determination, etc.) of any suitable types of nucleic acid molecules (e.g., DNA, RNA, cell-free DNA, cell-free RNA, nucleic acids from prenatal samples; etc.) and/or any other suitable types of molecules. Embodiments of the method 100 and/or system 200 can be applied to determine quantification (e.g., abundance determination) for any suitable biological targets, such as biological target sequences from different loci (e.g., of a same chromosome, of different chromosomes; etc.), which can facilitate relative abundance comparisons.

Figure 5A:
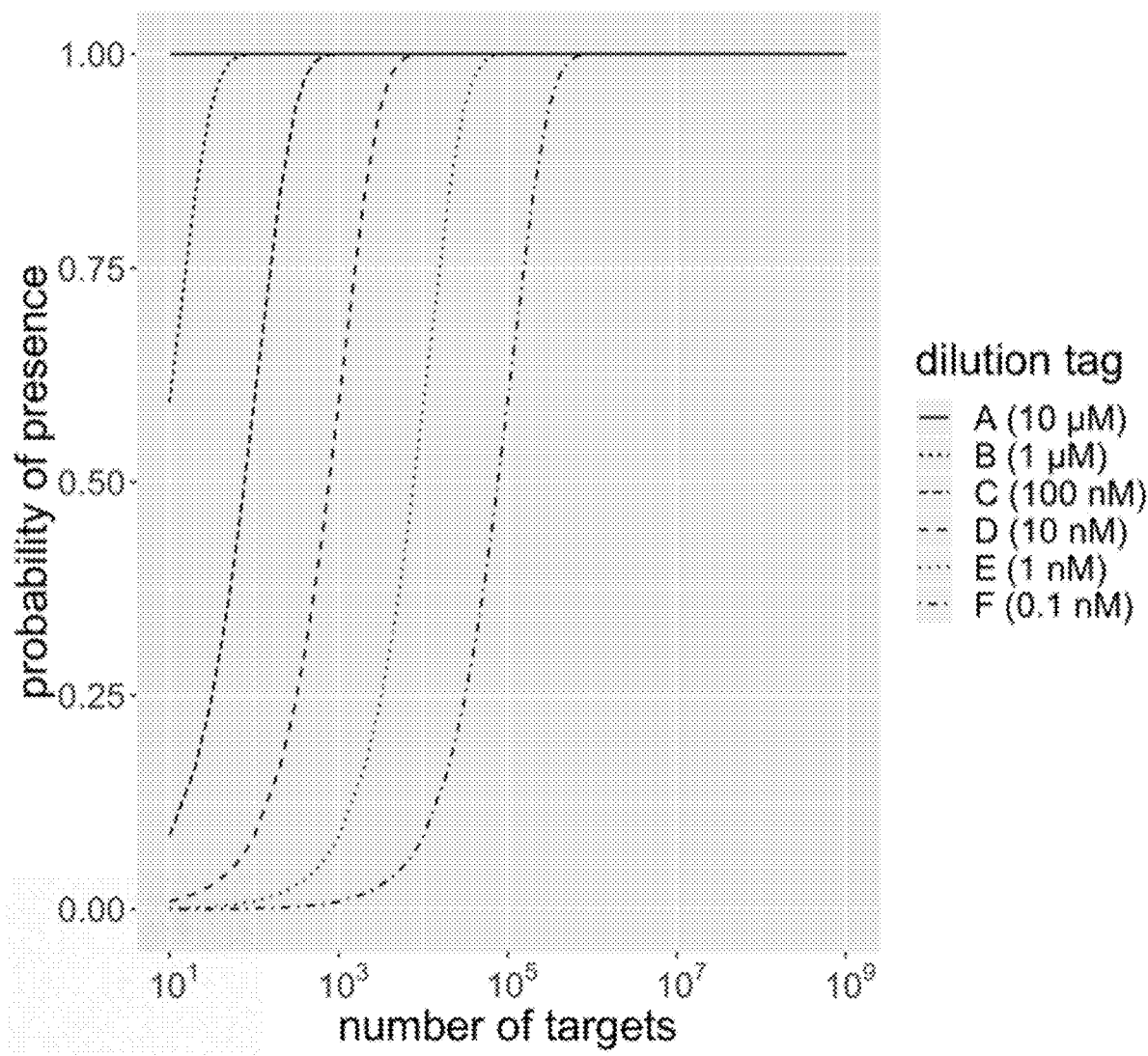
FIGS. 5A-5C include graph representations illustrating determining counts (e.g., number, etc.) of biological target molecules in a specific example of an embodiment of a method (e.g., for determining biological target abundance).
Figure 5B:
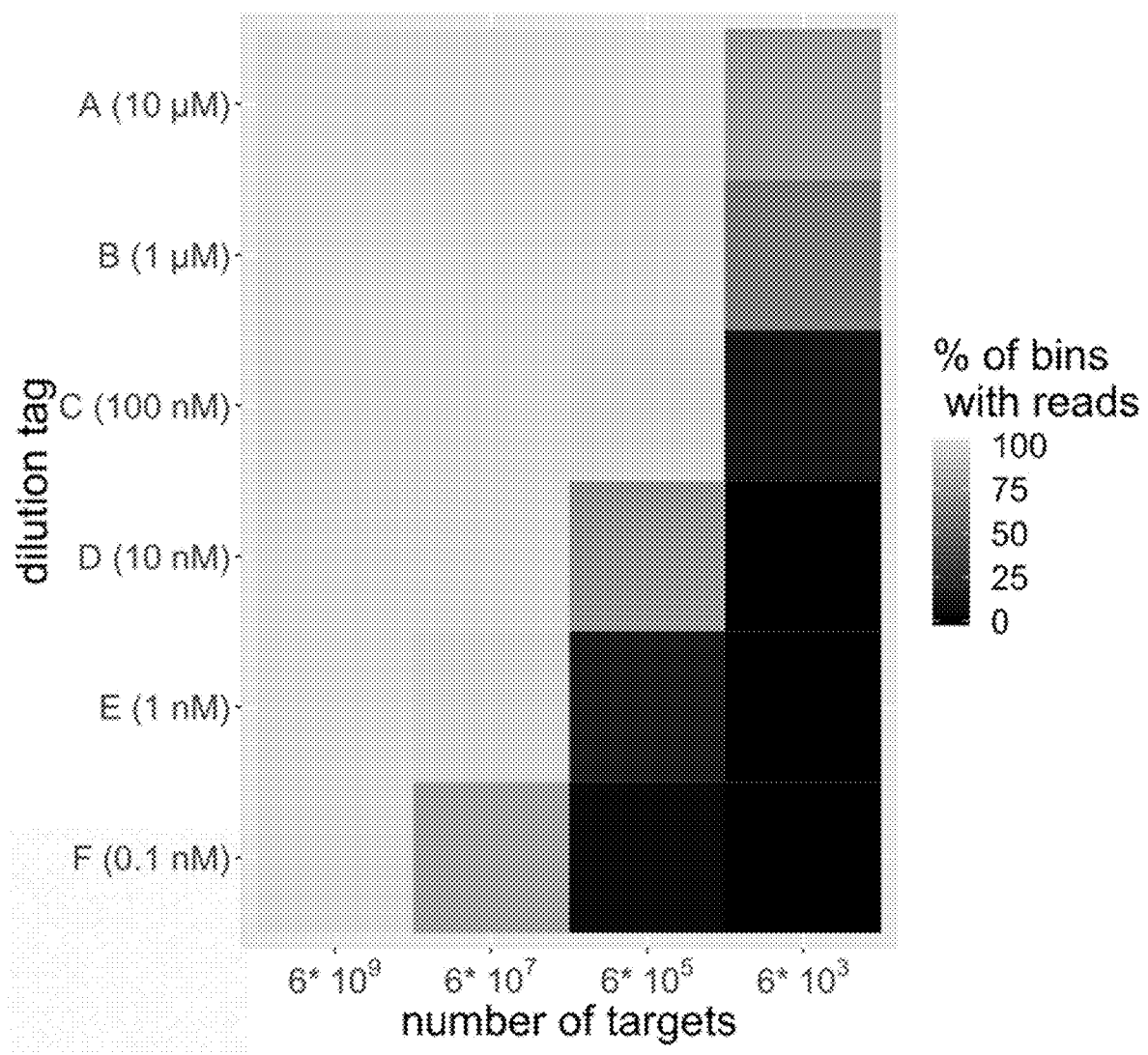
Figure 5C:
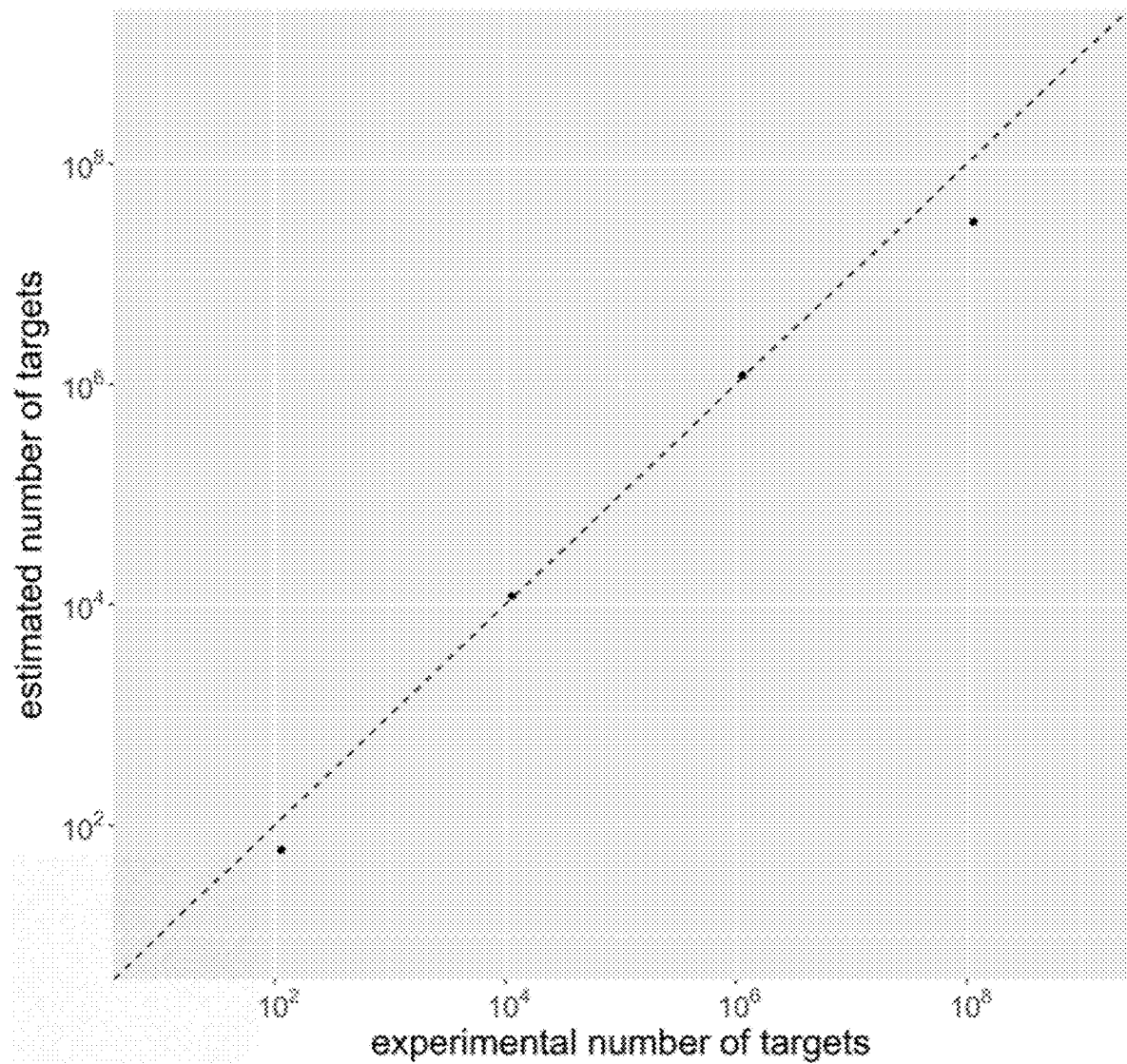

In specific examples, as shown in FIG. 5A.5C, portions of embodiments of the method 100 can be applied to accurately estimate counts of target molecules initially present in experimental samples. FIG. 5A includes a specific example of theoretical calculations for the probability of detecting the presence of dilution tags given a number of target molecules. FIG. 5B illustrates a specific heat map example of percentage of dilution tag bins with detected reads. FIG. 5C includes a specific example of combining results in FIG. 5B with the theoretical probabilities in FIG. 5A to estimate the number of target molecules that were initially present. However, any suitable concentrations of dilution tags (e.g., as part of oligonucleotides) can be used, and any suitable number of target molecules can be estimated using portions of embodiments of the method 100 and/or system 200.

Embodiments of the method 100 and/or system 200 can include and/or otherwise be used for characterization (e.g., diagnosis, etc.) and/or treatment (e.g., treatment determination, treatment evaluation and modification over time, etc.) in the context of one or more of: cancer (e.g., processing a liquid biopsy sample with an embodiment of the method 100 to evaluate the prevalence of circulating-tumor DNA over time in determining and/or evaluating treatments; targeting gene mutations associated with cancer, such as KRAS gene mutations and/or other suitable targets associated with oncogenes; etc.), noninvasive prenatal testing (NIPT) (e.g., in relation to genetic screening for any suitable chromosomal conditions, etc.), RNA-seq (e.g., for gene expression analysis over time; where target sequences in RNA samples can be relatively rare; etc.), exosome analysis, microbiome analysis (e.g., for targeting specific microbial biomarkers, such as a target 16S rRNA region; for targeting pathogenic microorganisms; etc.), pathogenesis (e.g., for evaluating the spread of antibiotic resistance in a population, etc.), food analysis (e.g., for identifying food that contains pathogenic microorganisms such as *Salmonella enterica*, etc.), environment analysis (e.g., for rapidly detecting the level of a particular gene product such as an antibiotic resistance gene; evaluating the species composition of an environmental sample that may be relevant for agriculture such as soil; for environmental monitoring applications over time to measure the ecological impact of industrial activity or climate change), immune system analysis (e.g., for evaluating progression of antibodies and associated receptors over time in relation to disease states; evaluating immunosuppressant treatment provision and/or risk of organ donor rejection based on relative amount of organ donor DNA in the blood stream over time; evaluating risk of graft-versus-host disease, such as in determining how and whether to provide treatment; etc.), and genetic disorders (e.g., gene amplification, gene deletion, partial chromosomal abnormalities, 22q11.2 deletion syndrome or DiGeorge syndrome, Charcot-Marie-Tooth syndrome, cystic fibrosis, Huntington's disease, Duchenne muscular dystrophy, sickle cell anemia, hemophilia, thalassemia, etc.). Applications can additionally or alternatively include: psychiatric and behavioral conditions (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); cardiovascular-related conditions (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; genetic-related conditions; chronic disease; and/or any other suitable type of applications.

Embodiments can additionally or alternatively transform entities (e.g., biological samples, targets, synthesized molecules, users, sample handling systems, computational systems, etc.) into different states or things. For example, the method 100 can include synthesis of oligonucleotides from constituent primers and dilution tags in order to process targets into forms suitable for improving efficiency of genetic sequencing (e.g., thereby improving the sequencing system) and count accuracy (e.g., thereby improving computer-related technology and the operation of the computer system itself) in enabling previously unperformable user condition characterizations and/or treatment evaluations (e.g., through facilitating meaningful count comparisons at practical costs). However, the embodiments can provide any other suitable benefit(s) in the context of using non-generalized systems for counting associated with target markers.

One or more instances and/or portions of the method 100 and/or processes described herein can be performed asynchronously (e.g., sequentially), concurrently (e.g., in parallel; concurrently processing biological samples in a multiplex, automated manner to determine a set of counts associated with one or more target sequences, users, and/or other suitable entities; concurrently computationally processing sequence reads to improve system processing ability; etc.), in temporal relation to a trigger event, and/or in any other suitable order at any suitable time and frequency by and/or using one or more instances of the system, components, and/or entities described herein. Embodiments of the system can include a sample handling network configured to synthesize molecules, process biological samples with the molecules, and/or perform other suitable processes; a sequencing system configured to sequence processed genetic material from the biological samples; a computing system configured to analyze the sequences; and/or any other suitable components. However, the method 100 and system 200 can be configured in any suitable manner.

Additionally or alternatively, data described herein (e.g., abundance metrics; counts, characterizations; models; ratios; identifiers; read depths; sequence reads; molecule designs such as oligonucleotide designs, primer designs, experiment designs; etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data described herein can be associated with value types including any one or more of: scores, binary values, classifications, confidence levels, identifiers (e.g., sample identifiers, molecule identifiers for any suitable molecules described herein, etc.), values along a spectrum, and/or any other suitable types of values. Any suitable types of data described herein can be used as inputs, generated as outputs, and/or manipulated in any suitable manner for any suitable components associated with embodiments of the method 100 and/or system 200.

Sequencing and/or sequencing-related technologies (e.g., in relation to sequencing of dilution tagged S130 and/or S140) associated with one or more portions of embodiments of the method 100 and/or system 200 (e.g., in relation to sequencing dilution tagged genetic targets; in association with sequencing primers; etc.) can include high throughput sequencing, which can include and/or be associated with any one or more of: NGS, NGS-associated technologies, massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing, sequencing-by-synthesis, tunneling currents sequencing, sequencing by hybridization, mass spectrometry sequencing, microscopy-based techniques, and/or any suitable technologies related to high throughput sequencing. Additionally or alternatively, sequencing and/or sequencing-related technologies can include and/or apply any suitable sequencing technologies (e.g., Sanger sequencing, capillary sequencing, any suitable sequencing technologies, etc.).

Embodiments of the method 100 and/or system 200 can be genetically or otherwise directly or indirectly encoded in biological systems (e.g. living cells such as bacteria, fungi, insect cell lines, mammalian cells lines, human cell lines, and model organisms, examples of which include, but are not limited to, *Drosophila melanogaster, Caenorhabditis elegans, Danio rerio*) for instance by attaching chemical or molecular tags (e.g. biotin, ubiquitin, maltose binding protein, MS2 coat binding protein, or any other element, metabolite, chemical, or protein product produced naturally or artificially in cells) either naturally present at varying concentrations in cells or engineered to be produced at various concentrations (for instance through the use of promoters of varying strength or any other method 100 of altering transcription, translation, production, of the molecular tag or conversion of the molecular tag to its active form) to any biological target molecules (e.g. nucleic acids, proteins, lipids, carbohydrates) in vivo within the cellular or biological system in conjunction with a modality for affinity purification of the molecular tag and associated entities, and/or with a system for detection of the molecular tag by chemical, fluorescent, or immunohistochemistry means, and/or with a system for quantifying or otherwise characterizing the amount or spatiotemporal distribution of the molecular tag using mass spectrometry, nuclear magnetic resonance, microscopy or any suitable technique, as a method to infer the relative abundances or threshold concentrations of one or many biological targets simultaneously (for instance, comparing the concentrations of two different proteins or identifying all proteins present in a cell within a range of concentrations).

Embodiments of the system 200 can include a sample handling network configured to generate molecules (e.g., first set of molecules; second set of molecules; etc.), process biological samples (e.g., cfDNA samples; etc.), facilitate generation of dilution tagged mixtures and/or perform other suitable processes; a sequencing system configured to sequence dilution tagged genetic targets and/or other suitable material; a computing system (e.g., remote computing system, local computing system, etc.) configured to analyze the sequences, to perform counting processes, to determine abundance metrics, to facilitate characterizations, and/or perform suitable computational processes; and/or any other suitable components. However, the method 100 and system 200 can be configured in any suitable manner.

2.1 Method—Generating a First Set of Molecules.

Generating a first set of molecules including a first set of dilution tags S110 can function to synthesize one or more molecules for processing with one or more biological samples, where the molecules can be identified by dilution tags associated with a concentration profile. The first set of molecules is preferably associated with (e.g., complementary to or otherwise having affinity to; targeting; able to be processed with; etc.) one or more target markers. Target markers preferably include target sequences (e.g., nucleic acid sequences indicative of a user condition; sequences including mutations, polymorphisms, etc.), but can additionally or alternatively include: proteins (e.g., serum proteins, antibodies, etc.), peptides, carbohydrates, lipids, other nucleic acids (e.g., extracellular RNA, microRNA, messenger RNA, where abundance determination for RNA targets can include suitable reverse transcriptase operations, etc.), whole cells, metabolites, pharmacologic agents, natural products, genetic predisposition biomarkers, diagnostic biomarkers, prognostic biomarkers, predictive biomarkers, other molecular biomarkers, gene expression markers, imaging biomarkers, and/or other suitable markers. Target markers are preferably associated with applications described herein, and can additionally or alternatively be associated with one or more user conditions including: symptoms, causes, diseases, disorders, and/or any other suitable aspects associated with conditions. For example, the method 100 can include generating a first subset of molecules including forward primers and second subset of molecules including reverse primers, where the primers target a mutation in the KRAS oncogene.

The molecules preferably include one or more oligonucleotides. The oligonucleotides (and/or other molecule types) can include one or more: primers, dilution tags, bin identifiers, sequencing molecules (e.g., sequencing primers configured to facilitate operation of sequencing systems; etc.), probes, components for introducing mutations and/or restriction sites, types of RNA (e.g., antisense RNA, small interfering RNA, etc.), and/or other suitable components. As such, each molecule of the set of molecules can include a plurality of identifiers (e.g., including a dilution tag, a bin identifier, a primer acting as an identifier, etc.) including different types of information. In an example, as shown in FIGS. 2 and 4A, generating a set of molecules can include synthesizing: a first subset of oligonucleotides where each includes a forward primer (e.g., that anneals to a target sequence), a dilution tag from a set of dilution tags, and a bin identifier from a set of bin identifiers; and a second subset of oligonucleotides where each includes a reverse primer (e.g., that anneals to the complementary strand for the target sequence), a dilution tag from the set of dilution tags, and a bin identifier from the set of bin identifiers. In a specific example, the different subsets of oligonucleotides (e.g., of a first set of oligonucleotides; etc.) include forward primer subsets and reverse primer subsets, where oligonucleotides of a forward primer subset of the forward primer subsets include: a dilution tag unique to the first subset of the different subsets of oligonucleotides; and a forward primer region for annealing to a strand associated with the target sequence; where oligonucleotides of a reverse primer subset of the reverse primer subsets include: a dilution tag unique to the second subset of the different subsets of oligonucleotides; and a reverse primer region annealing to a complementary strand associated with the target sequence; and where generating the first set of oligonucleotides includes generating the first set of oligonucleotides at predetermined relative concentrations that are different for at least one of: the forward primer subsets and the reverse primer subsets. In a specific example, the forward primer subsets and reverse primer subsets are at different relative concentrations. In a specific example, the forward primer subsets can include different relative concentrations, while the reverse primer subsets are kept at substantially similar concentration; or vice versa. In another example, the synthesized oligonucleotides are each 15-25 bases in length, but the oligonucleotides (and/or other suitable components described herein, such as target sequences, dilution tagged mixture components, etc.) can possess any suitable length (e.g., any suitable number of bases).

Each molecule of the set of molecules preferably includes one or more dilution tags. The dilution tags preferably indicate a concentration (e.g., a relative concentration relative other dilution tags; an absolute concentration; etc.) associated with molecules tagged with the dilution tag. In an example, pairs of dilution tags (e.g., a first dilution tag of a first oligonucleotide including a forward primer for a target sequence, and a second dilution tag of a second oligonucleotide including a reverse primer for the target sequence, etc.) are processed to achieve predetermined concentrations (e.g., for subsets of dilution tagged genetic targets in a dilution tagged mixture) relative to other pairs of dilution tags (e.g., other pair permutations for the set of dilution tags), such as according to a relative concentration profile, as shown in FIGS. 2 and 4B. In another specific example, individual dilution tags are processed to achieve relative concentrations to other individual dilution tags. However, concentration information can be associated with any suitable number or combination of dilution tags (e.g., a single dilution tag, a pair, at least three, etc.). Dilution tags are preferably nucleotide sequences mapped to concentration information (e.g., included in a relative concentration profile), but can be of any suitable component type described herein. However, dilution tags can be configured in any suitable manner.

In a variation, molecules of the set of molecules (e.g., a first set of molecules, a second set of molecules; etc.) can include one or more bin identifiers (e.g., as shown in FIG. 4A, 4C; etc.). Bin identifiers preferably facilitate (e.g., during computational post-processing) grouping of dilution tagged genetic targets (and/or other components) into bins (e.g., where a count can be determined for each bin, and an overall count can be determined by averaging the individual counts associated with the bins, etc.), such as to improve count accuracy (e.g., through leveraging a plurality of individual count measurements to determine an overall count of greater accuracy, etc.), but can additionally or alternatively facilitate any other suitable process and/or goal. A bin identifier preferably includes a randomized sequence. For example the bin identifier can include an N randomized sequence including one or more "N" nucleotides, where "N" can be one of the biological nucleotides (e.g., A, C, G, and T for a DNA-based molecule) at equal probability (or at any suitable probability distribution across the different nucleotides). In a specific example, each molecule can include a bin identifier of a "NNNN" randomized sequence for enabling binning into up to $4^4$ bins (e.g., bins corresponding to "AAAA", "AAAT", "AAAC", "AAAG", and the other permutations of nucleotides for an "NNNN" sequence in equal proportions). Additionally or alternatively, the bin identifier can include a non-randomized sequence (e.g., predetermined sequences). Bin identifiers can facilitate any suitable number of bins for improving count determination. In an example, determining bin identifiers can include selecting a number of bins based on an expected count (e.g., selecting a number of bins to enable each bin to be associated with sufficient sequencing depth; selecting a number of "N" nucleotides that enables a number of bins that exceeds the expected count, such that dynamic range and/or accuracy can be optimized by combining bins in computational post-processing); and determining bin identifiers (e.g., specific sequences) based on the selected number of bins. However, bin identifiers can be configured in any suitable manner.

In another variation, molecules of the set of molecules can include one or more sequencing molecules configured to aid in the operation of sequencing systems. The sequencing molecules preferably include sequencing primers (e.g., Sequencing Primer 1 and Sequencing Primer 2 for facilitating paired end sequencing on Illumina sequencing systems), but can additionally or alternatively include adapter sequences, and/or other suitable components associated with any suitable sequencing systems (e.g., Nanopore sequencing systems; sequencing systems associated with any suitable sequencing quality scores; sequencing systems used for any suitable applications described herein, such as RNA-seq; etc.). However, sequencing molecules can be configured in any suitable manner.

Generating the molecules can include synthesizing the molecules through performing any one or more of: a phosphoramidite approach, post-synthetic processing, purification (e.g., using high-performance liquid chromatography or other chromatography approaches, desalting, washing, centrifuging, etc.), amplification techniques (e.g., polymerase chain reaction), plasmid-based nucleic acid synthesis, other gene synthesis techniques, and/or any suitable sample processing technique. The set of molecules can be generated for processing with multiple biological samples (e.g., concurrently synthesizing a batch of molecules for use with samples across multiple users, to improve efficiency of the sample handling system) associated with multiple target sequences. Additionally or alternatively, any suitable number of molecules and/or types of molecules can be generated at any suitable time and frequency.

However, generating molecules including dilution tags S110 can be performed in any suitable manner.

2.2 Method—Generating a Second Set of Molecules.

Generating a second set of molecules S120 including a second set of dilution tags associated with the first set of dilution tags can function to generate a second set of molecules that can be processed (e.g., used in PCR, etc.) with products generated in relation to the first set of molecules (e.g., dilution tagged genetic targets), and/or that can be processed with any suitable components. Generating the second set of molecules can be performed in any manner analogous to generating the first set of molecules (e.g., molecules of the second set of molecules can include any analogous components, etc.). In an example, as shown in FIGS. 2 and 4C, generating the second set of molecules can include synthesizing: a first subset of oligonucleotides where each includes a forward primer targeting a dilution tag of a molecule (e.g., an oligonucleotide including a forward primer targeting the target sequence) from the first set of molecules, and a sequencing molecule (e.g., Sequencing Primer 1); and a second subset of oligonucleotides where each includes a reverse primer targeting a dilution tag of a molecule (e.g., an oligonucleotide including a reverse primer targeting the target sequence) from the first set of molecules. In a specific example, different subsets of molecules can be generated for each of the different types of dilution tags (e.g., different subsets of oligonucleotides, where each subset includes a different primer targeting a different dilution tag type).

In examples, the second set of molecules (e.g., oligonucleotides, etc.) include sequencing primers (e.g. sequencing primers and/or sequencing primer regions described herein; etc.) for facilitating high throughput sequencing of the different subsets of dilution tagged genetic targets.

However, generating the second set of molecules S120 can be performed in any suitable manner (or omitted, as can any other suitable portion of the method 100).

2.3 Method—Generating a Dilution Tagged Mixture.

Generating a dilution tagged mixture S130 based on processing the first set of molecules with targets from a biological sample can function to label (e.g., tag, etc.) the biological sample (e.g., genetic targets from the biological sample) with dilution tags from the first set of molecules. Generating the dilution tagged mixture can additionally or alternatively function to amplify components of the biological sample, pre-process the biological sample (e.g., sample preparation, lysis, bead-based processes, other purification and/or nucleic acid extraction techniques, etc.), and/or process the biological sample in any suitable manner. The method 100 can include collecting one or more biological samples (e.g., in a sample container provided to a user in a sample collection kit), which can include any one or more of: blood, plasma, serum, tissue, biopsies, sweat, urine, feces, semen, vaginal discharges, tears, interstitial fluid, other body fluid, and/or any other suitable samples (e.g., associated with a human user, animal, object such as food, microorganisms, etc.). The biological sample can include components from multiple users (e.g., a blood sample including nucleic acids from a mother and nucleic acids from the mother's unborn baby), components collected across multiple time periods, and/or components varying across any suitable condition, such that generating dilution tagged mixture(s) can be performed for any suitable number and type of entities. Targets preferably include one or more target sequences (e.g., where the genetic targets are DNA molecules including the target sequence), but generating the dilution tagged mixture (and/or other portions of the method 100) can additionally or alternatively be for any suitable target type (e.g., target marker types described herein).

Generating the dilution tagged mixture preferably includes tagging sample components with one or more dilution tags, such as through primer extension or ligation or other suitable tagging methods. In an example, the generated dilution tagged mixture can include different subsets of dilution tagged genetic targets identified by different dilution tag pairs ($D_i^F$, $D_j^R$), where the biological sample is processed with the first set of molecules to obtain the different subsets of dilution tagged genetic targets at a predetermined relative concentration profile. In a specific example, as shown in FIGS. 2 and 4A-4B, the first set of molecules can include a first subset of four dilution tag types associated with a forward primer, and a second subset of four dilution tag types associated with a reverse primer, where processing the first set of molecules with the biological sample can result in a dilution tagged mixture including a different subset of dilution tagged genetic targets for each permutation of dilution tag pair (e.g., a dilution tag pair including one of the four dilution tags associated with a forward primer, and including one of the four dilution tags associated with a reverse primer). Alternatively, dilution tag pairs (and/or other dilution tag combinations) can be independent from primer type (e.g., independent from whether the primer is a forward or reverse primer). However, the dilution tagged mixture can include any suitable number of types of dilution tagged genetic targets at any suitable concentration.

In another example, generating the subsets of dilution tagged genetic targets includes performing two rounds (or any suitable number of rounds) of PCR to anneal the forward and reverse primers of the first set of molecules to the target sequence. Additionally or alternatively, tagging sample components with dilution tags can be performed with any one or more: ligation techniques (e.g., sticky-end ligation; blunt-end ligation; ligation with DNA ligases such as Taq ligase, $T_4$ ligase, $T_3$ ligase, $T_7$ ligase, and/or other suitable ligases; ligation with RNA ligases; topoisomerase-mediated ligation; etc.), tagmentation techniques (e.g., where DNA and/or other suitable nucleic acid molecules are cleaved and tagged), tagging techniques (e.g., molecular tagging techniques, fluorescent tagging techniques, particle labeling techniques, etc.), capture by circularization approaches (e.g., molecular inversion probe, where synthesized molecules can include single-stranded probes including dilution tags facilitating abundance determination; gene selector; capture by selective circularization; etc.), other genomic partitioning techniques, and/or any other suitable techniques. In an example, generating the dilution tagged mixture includes tagging target molecules with the different dilution tags based on at least one of: a PCR-based technique, a ligation technique, and a tagmentation technique. In an example of applying ligation techniques, the method 100 can include: synthesizing a set of molecules including dilution tags and bin identifiers (e.g., where primers are omitted from the synthesized molecules); ligating the set of molecules to targets (e.g., DNA targets) from the biological sample using one or more ligation techniques; performing massively parallel quantitative PCR (qPCR) and/or suitable amplification techniques for the ligation-processed targets; and determining abundance metrics based on the ligation-processed targets. In relation to applying ligation techniques (and/or other suitable techniques) in the context of dilution tagging, applications can include: 16S metagenomics, RNA-seq, exosome RNA sequencing, sequencing associated with adaptive immunity, and/or other suitable applications described herein.

Generating the dilution tagged mixture can include labeling one or more genetic targets from the biological sample, such as through processes performed for tagging the genetic targets with dilution tags. In examples, labeling can include performing one or more of: PCR-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and/or any other suitable amplification techniques and/or associated protocol. In a specific example, generating the dilution tagged mixture can include performing a first PCR process with the first set of molecules and a sample (e.g., cfDNA sample), where the first set of molecules include primer regions complementary to a target sequence associated with the biological target; and performing a second PCR process (e.g., PCR amplification process, etc.) with a second set of molecules including dilution tag-associated primer regions complementary to nucleotide sequences of the different dilution tags. In variations, performing a PCR-based labeling process can include performing an PCR amplification process.

However, generating a dilution tagged mixture S130 can be performed in any suitable manner.

2.4 Method—Amplifying the Dilution Tagged Mixture.

Amplifying the subsets of dilution tagged targets S140 using the second set of molecules can function to generate copies of the dilution tagged targets. Amplification can be through sample processing techniques described herein (e.g., multiple rounds of PCR), or any suitable techniques. Amplifying the subsets of dilution tagged genetic targets preferably includes separately amplifying the different subsets of dilution tagged targets (e.g., amplifying the different subsets with different PCR operations, such as in separate containers). For example, amplifying the dilution tagged mixture can include subsampling the dilution tagged mixture into subsamples (e.g., where the number of subsamples corresponds to the number of subsets of dilution tagged targets selected for amplification, etc.); associating each subsample with a different subset of dilution tagged target (e.g., associating a first subsample to a first dilution tag pair such as $D_0^F$, $D_0^R$, associating a second subsample to a second dilution tag pair such as $D_0^F$, $D_1^R$, etc.); and for each subsample, performing amplification with molecules (e.g., from the second set of molecules) configured for amplifying the corresponding subset of dilution tagged targets (e.g., processing the first subsample with molecules including primers targeting sequences for the $D_0^F$, $D_0^R$ dilution tag pair, etc.), but subsampling and associated processing can be performed in any suitable manner. In a specific example, separately amplifying the different subsets of dilution tagged genetic targets can include subsampling the dilution tagged mixture into subsamples; associating each subsample with at least one dilution tag combination of the different tag combinations; and for each subsample, performing amplification with dilution tag combination-specific oligonucleotides of the second set of oligonucleotides, where the dilution tag combination-specific oligonucleotides are configured for amplifying dilution tagged genetic targets associated with the at least one dilution tag combination associated with the subsample. Leveraging primers targeting the dilution tag sequences from the first set of molecules can confer improvements in count accuracy and count comparisons (e.g., where the same primer type targeting the same dilution tag sequence can be used for different amplification operations for different biological samples, for different target sequences, etc.; where using the same primer types across different instances of the method 100 can enable amplification at similar rates across the different instances; etc.). Alternatively, amplifying the different subsets of dilution tagged targets can be performed in a combined manner (e.g., in a single container). However, different components of the dilution tagged mixture can be amplified in any suitable combination in any suitable manner.

Amplifying the subsets of dilution tagged targets can include selecting a subgroup of the subsets to amplify (e.g., as opposed to amplifying every subset). In an example, selecting the subgroup of subsets can include selecting a subgroup of dilution tag pair types representing each of the possible relative concentrations in the relative concentration profile (e.g., selecting the bolded dilution tag pairs in the relative concentration profile shown in FIGS. 2 and 4B), such as without selecting any dilution tag pair types that would act as a repeat of a relative concentration already represented in the subgroup. Alternatively, every subset of dilution tagged targets can be amplified. However, amplifying the subsets of dilution tagged targets S140 can be performed in any suitable manner.

2.5 Method—Generating a Modified Dilution Tagged Mixture

Generating a modified dilution tagged mixture S150 based on the relative concentration profile (e.g., describing the relative concentrations of the amplified different subsets of dilution tagged targets) can function to generate a modified mixture that includes the subsets of dilution tagged targets at a modified relative concentration profile (e.g., achievable through knowing the relative concentrations of the components used in generating the modified dilution tagged mixture; a modified relative concentration profile configured to enable improved dynamic range; etc.). The modified relative concentration profile is preferably an equalized concentration profile with the different subsets of dilution tagged targets at substantially equal concentrations, but can alternatively include any suitable concentration profile (e.g., relative concentration profile, absolute concentration profile, etc.) with any suitable concentration distribution across components of the mixture. In an example, generating the modified dilution tagged mixture can include: determining the amounts of each amplified subsample of the dilution tagged mixture to combine to achieve a desired modified relative concentration profile for the modified dilution tagged mixture, given the known relative concentration profile for the subsamples (e.g., corresponding to the relative concentrations for the different subsets of dilution tagged genetic targets, etc.). Additionally or alternatively, the known relative concentration profile of the constituents of the modified dilution tagged mixture can be used in any suitable manner to process the constituents in generating the modified dilution tagged mixture. In examples, generating the modified dilatation tagged mixture and/or other portions of the method 100 can include selecting sample processing protocols based on optimizing number of optimizations, difficulty, time requirements, margin of error, desired outputs, and/or any other suitable parameters. In a specific example, generating a modified dilution tagged mixture can include: measuring the DNA abundance (e.g., DNA mass) in each amplified subsample of the dilution tagged mixture (e.g., through Nanodrop UV-vis spectrophotometry; through using a Qubit DNA fluorometer, etc.); and combining the amplified subsamples into a modified dilution tagged mixture based on the measured DNA abundances (e.g., where the modified dilution tagged mixture possesses an equalized mass profile with equal or substantially equal mass for each of the different subsets of dilution tagged targets, etc.). However, generating the modified dilution tagged mixture S150 can be performed in any suitable manner.

2.6 Method—Determining an Abundance for a Biological Target.

Figure 3:
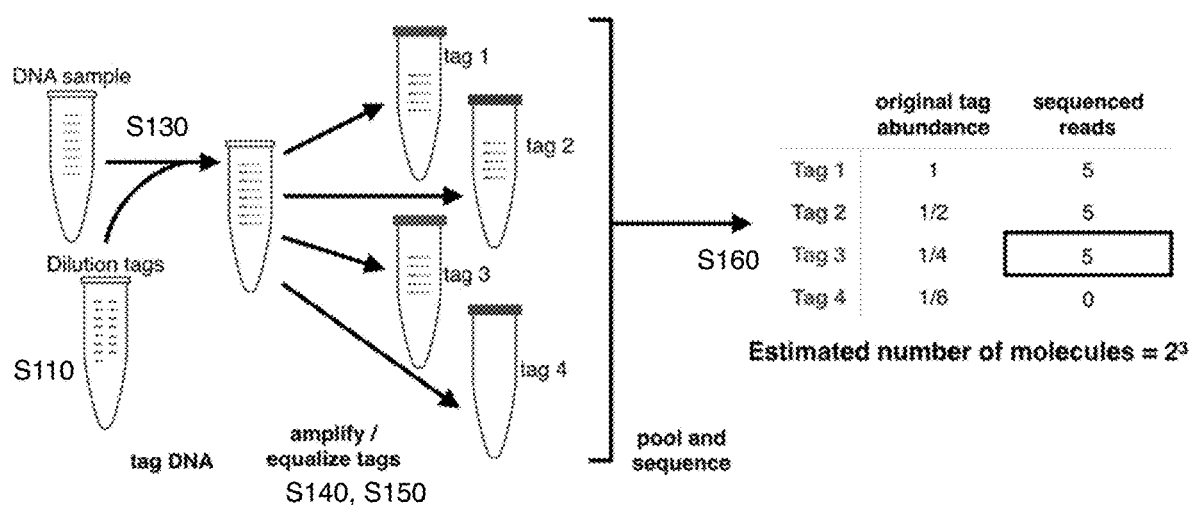
FIG. 3 includes a schematic representation of a variation of dilution tagging and determining target count.

Determining one or more counts (and/or other measures of abundance) of the distinct targets (e.g., distinct DNA molecules including a target sequence) S160 based on analysis of the modified dilution tagged mixture can function to accurately estimate a target count in the biological sample, such as by identifying the limiting dilution (e.g., dilution tag combination of greatest relative concentration while being detected at a level below a threshold detection level, such as being one or more of undetected, having a detection level sufficiently below a reference detection level associated with a different dilution tag pair, having a detection level below a predetermined reference detection level, having a number of reads below a threshold number, having a low number of reads relative reads for a different dilution tag pair; etc.), which can correspond to an estimated number of target molecules (e.g., as shown in FIG. 3). As such, embodiments of the method can enable logarithmic-based counting (e.g., logarithmic counting, Log Log counting, Hyper Log Log counting, etc.) and/or other suitable improvements in abundance determination. In a specific example, determining the count of the distinct target molecules based on the equalized dilution tagged mixture and the relative concentration profile includes: identifying a limiting dilution based on sequencing of the equalized dilution tagged mixture; and determining the count of the distinct target molecules based on the limiting dilution and the relative concentration profile associated with the different dilution tag pairs. In a specific example, identifying the limiting dilution includes: determining sequence reads corresponding to the different dilution tag pairs based on comparing nucleotide sequences of the sequence reads to nucleotide sequences of the different dilution tag pairs, and identifying the dilution tag pair of greatest relative concentration while not being detected in the sequence reads; and where determining the count of the distinct target molecules includes determining the count based on a relative concentration indicated by the relative concentration profile for the identified dilution tag pair.

The analysis of the modified dilution tagged mixture preferably includes sequencing of the modified dilution tagged mixture (and/or a processed form of the modified dilution tagged mixture); computationally processing the sequence read results; and/or any other suitable processes. For example, as shown in FIG. 3, determining a count can include: for each dilution tag pair (or other dilution tag combination), identifying the number of sequence reads corresponding to the dilution tag pair (e.g., based on comparing the nucleotide sequence of the sequence read to a nucleotide sequence for the dilution tag pair); identifying the dilution tag pair of greatest relative concentration while having no sequence reads; and determining a count based on the relative concentration indicated by the identified dilution tag pair. Additionally or alternatively, determining a count can include applying a count determination model including any one or more of: probabilistic properties, heuristic properties, deterministic properties, and/or any other suitable properties.

In a variation, determining abundance of a target can include determining an overall count from a plurality of individual counts (e.g., for different groupings of the distinct target molecules. Etc.), which can function to increase accuracy of the count estimation. Determining an overall count is preferably based on a binning approach. For example, as shown in FIG. 2, dilution tagged targets can include bin identifiers from the molecules (e.g., molecules including primers) used to process (e.g., primer extension, amplification, etc.) the targets, where determining an overall count can include: grouping the dilution tagged targets (e.g., grouping the corresponding sequence reads) into the bin identified by their corresponding bin tags; for each bin, determining an individual count based on the dilution tagged targets associated with the bin; and determining an overall count based on the individual counts (e.g., averaging the individual counts; determining the median; etc.). In a specific example, determining the overall count based on the plurality of individual counts includes: determining the different groupings of the distinct target molecules based on bin identifiers associated with the different subsets of dilution tagged genetic targets; and for each grouping of the different groupings, determining an individual count of the plurality of individual counts based on the relative concentration profile associated with the different dilution tag combinations corresponding to the grouping.

Additionally or alternatively, determining an overall abundance from individual abundances can leverage any suitable statistical approach and can be performed in any suitable manner.

In another variation, determining counts can include applying different count determination models (e.g., count determination using different relative concentration profiles; different sample processing steps; different dilution tags, bin identifiers, primers; etc.) for different applications (e.g., applying a different model for human nucleic acid target sequences versus microbial nucleic acid target sequences; applying a different model for NIPT versus cancer screening; etc.), biological samples (e.g., different parameters for portions of the method 100 based on collection site of the biological sample; different parameters based on different user demographics; different parameters for biological samples collected at different time periods; etc.), and/or any other suitable differences in conditions. However, determining abundance of a target S160 can be performed in any suitable manner.

2.7 Method—Quantitatively Comparing Abundances

The method 100 can additionally or alternatively include quantitatively comparing different counts S170, which can function to determine meaningful comparisons between counts estimated by portions of the method 100 (and/or other suitable approaches). Comparing different counts can be for one or more of: counts determined for different time periods, different targets (e.g., for different target sequences), different users (e.g., enabling comparisons for different user demographics, for different user behaviors, etc.), different biological samples (e.g., different types of biological samples), and/or for any difference in conditions. For example, determining and analyzing counts of a target (e.g., an oncogene target mutation present in circulating-tumor DNA) can be performed over the course of a treatment regimen, where the analysis of target counts over time can be used in determining treatment efficacy (e.g., treatment response, etc.), recommending and/or updating treatments, characterizing a status of the user condition, and/or performing any other suitable treatment-related process. In an example, a first abundance of the biological target (e.g., determined using any suitable portions of the method 100; etc.) is associated with a first time period, where the method 100 can further include determining a subsequent abundance of the biological target based on a subsequent modified dilution tagged mixture and the relative concentration profile, where the subsequent abundance of the biological target is associated with a second time period, such as where the abundance associated with the first time period and the abundance associated with the second time period are configured for facilitating characterization of a condition. In a specific example, the biological target is associated with a cancer condition, and where the abundance associated with the first time period and the abundance associated with the second time period are configured for facilitating characterization of a treatment response for the cancer condition.

In another example, embodiments of the method 100 can be frequently applied (e.g., during checkups with care providers) to determine counts over time for target markers associated with different user conditions, where the embodiments can facilitate routine diagnostic screening. However, quantitatively comparing abundances S170 can be performed in any suitable manner.

2.8 Method—Providing a Treatment

The method 100 can additionally or alternatively include providing a treatment S180 based on one or more counts, which can function to leverage count data to determine and/or otherwise facilitate personalized treatment provision. Treatments can include any one or more of: therapeutic compositions (e.g., pregnancy-related compositions, medication-based treatments, probiotic-based treatments, topical-based treatments, etc.), medical device-based treatments, health-related notifications (e.g., transmitted to the subject, to a care provider, etc.) including user condition-related and/or treatment-related information derived based on the abundance data (e.g., count data); diet-related treatments; cognitive/behavioral treatments; physical therapies; clinical-related treatments (e.g., telemedicine, scheduling a care provider appointment, etc.); alternative medicine-based treatments; environmental-based treatments; and/or any other suitable type of treatments.

In a variation, providing a treatment can be exclusively based on abundance data. For example, providing a treatment can be in response to the count satisfying a threshold condition (e.g., a count exceeding a threshold count for a particular target; a count indicating a risk of a user condition beyond a threshold risk; etc.). In a specific example, in response to the count satisfying a threshold condition, providing a treatment can include notifying a care provider, scheduling a care provider appointment, facilitating a digital telemedicine communication, and/or performing any other suitable action to facilitate treatment provision.

In another variation providing a treatment can be based on abundance data and supplementary data, which can include any one or more of: biometric data (e.g., sampled at a supplementary medical device), medical history data, family medical history, demographic data, genetic history, microbiome data, and/or any other suitable data associated with contextualizing the abundance data. For example, the method 100 can include providing a series of treatments for a user condition over time, such as through iteratively updating a treatment regimen (e.g., adjusting medication dosage, medication type, etc.) based on counts determined over time for targets associated with the user condition. However, providing treatments S180 can be performed in any suitable manner. However, portions of embodiments of the method 100 can be performed in any suitable manner.

3. Other.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with embodiments of the system 200. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

We claim:

1. A method for determination of abundance of a nucleic acid target from a sample including cell-free DNA (cfDNA), the method comprising:
    generating a first set of oligonucleotides comprising different subsets of oligonucleotides, wherein each subset of the different subsets of oligonucleotides comprises oligonucleotides comprising:
        a dilution tag sequence associated with the subset of the different subsets of oligonucleotides, wherein the dilution tag sequence is associated with a relative concentration profile indicating different relative concentrations of different dilution tag sequence combinations, and
        a target-specific region complementary to a target sequence of the nucleic acid target;
    generating a second set of oligonucleotides comprising dilution tag sequence-associated regions complementary to nucleotide sequences of the dilution tag sequences of the first set of oligonucleotides;
    performing a labeling process with the first set of oligonucleotides and the cfDNA from the sample, thereby generating a dilution-tagged mixture comprising different subsets of the dilution-tagged nucleic acid target identified by the different dilution tag sequence combinations at different relative concentrations indicated by the relative concentration profile;
    performing an amplification process with the second set of oligonucleotides and the dilution-tagged mixture;
    modifying concentrations of the different subsets of the amplified dilution-tagged mixture to generate a modified dilution-tagged mixture; and
    determining an abundance of the nucleic acid target using the modified dilution-tagged mixture and the relative concentration profile associated with the different dilution tag sequence combinations.

2. The method of claim 1, wherein performing the amplification process comprises separately amplifying the different subsets of the dilution-tagged nucleic acid target.

3. The method of claim 2, wherein separately amplifying the different subsets of the dilution-tagged nucleic acid target comprises subsampling the dilution-tagged mixture into subsamples;
associating each subsample with at least one dilution tag sequence combination of the different tag combinations; and
for each subsample, performing amplification with dilution tag sequence combination-specific oligonucleotides of the second set of oligonucleotides, wherein the dilution tag sequence combination-specific oligonucleotides are configured for amplifying the dilution-tagged nucleic acid target associated with the at least one dilution tag sequence combination associated with the subsample.

4. The method of claim 3, wherein generating the modified dilution-tagged mixture comprises determining the amounts of each amplified subsample of the dilution-tagged mixture to combine based on the relative concentration profile associated with the different dilution tag sequence combinations.

5. The method of claim 1, wherein determining the abundance of the nucleic acid target comprises determining an overall count of distinct target molecules based on a plurality of individual counts for different groupings of the distinct target molecules.

6. The method of claim 5, wherein determining the overall count based on the plurality of individual counts comprises:
    determining the different groupings of the distinct target molecules based on bin identifiers associated with the different subsets of the dilution-tagged nucleic acid target; and
    for each grouping of the different groupings, determining an individual count of the plurality of individual counts based on the relative concentration profile associated with the different dilution tag sequence combinations corresponding to the grouping.

7. The method of claim 6, wherein the oligonucleotides of the different subsets of oligonucleotides comprise the bin identifiers, and wherein each bin identifier of the bin identifiers comprises a randomized nucleotide sequence.

8. The method of claim 1, wherein:
    the abundance of the nucleic acid target is a relative abundance relative to other nucleic acid targets;
    the other nucleic acid targets each have corresponding different subsets of oligonucleotides that are at predetermined relative concentrations based on a relative concentration profile;
    the target-specific region for each nucleic acid target is a primer region complementary to a target sequence of the nucleic acid target;
    the modified dilution-tagged mixture is an equalized dilution-tagged mixture comprising the different subsets of dilution-tagged nucleic acid targets at substantially equal concentrations based on the relative concentration profile associated with the dilution tag sequence combinations, and
    the method further comprises:
        determining a count of target molecules corresponding to the nucleic acid target based on the equalized dilution-tagged mixture and the relative concentration profile associated with the dilution tag sequence combinations to determine the relative abundance of the nucleic acid target and the other nucleic acid targets based on the counts for the nucleic acid targets.

9. The method of claim 8, wherein determining the abundance of the nucleic acid target facilitates characterization of a cancer.

10. The method of claim 9, wherein the cancer is associated with an ERBB2 gene.

11. The method of claim 8,
wherein the different subsets of oligonucleotides comprise forward primer subsets and reverse primer subsets,
wherein oligonucleotides of a forward primer subset of the forward primer subsets comprise:
a dilution tag sequence unique to the first subset of the different subsets of oligonucleotides; and
a forward primer region for annealing to a strand of the target sequence;
wherein oligonucleotides of a reverse primer subset of the reverse primer subsets comprise:
a dilution tag sequence unique to the second subset of the different subsets of oligonucleotides; and
a reverse primer region annealing to a complementary strand of the target sequence; and
wherein generating the first set of oligonucleotides comprises generating the first set of oligonucleotides at predetermined relative concentrations that are different for at least one of: the forward primer subsets and the reverse primer subsets.

12. The method of claim 8, wherein the second set of oligonucleotides comprises sequencing primers for facilitating high-throughput sequencing of the different subsets of dilution-tagged nucleic acid targets.

13. The method of claim 1, wherein the abundance of the nucleic acid target is a relative abundance.

14. The method of claim 1, wherein the modified dilution-tagged mixture is an equalized dilution-tagged mixture.

15. A method for determination of abundance of a biological target, the method comprising:
generating a first set of molecules comprising different subsets of molecules comprising different dilution tags associated with the different subsets of molecules, wherein the different dilution tags are associated with a relative concentration profile indicating different relative concentrations associated with the different dilution tags;
generating, using the first set of molecules and the biological target, a dilution-tagged mixture comprising different subsets of the dilution-tagged biological target comprising the different dilution tags associated with the different relative concentrations indicated by the relative concentration profile;
modifying concentrations of the different subsets of the dilution-tagged mixture to generate a modified dilution-tagged mixture; and
determining an abundance of the biological target using the modified dilution-tagged mixture and the relative concentration profile.

16. The method of claim 15, wherein the different dilution tags are nucleic acids and generating the dilution-tagged mixture comprises tagging target molecules with the different dilution tags using at least one of: a PCR technique, a ligation technique, and a tagmentation technique.

17. The method of claim 16, wherein the different dilution tags are nucleic acids and generating the dilution-tagged mixture comprises:
performing a first PCR process with the first set of molecules and the biological target, wherein the first set of molecules comprises primer regions complementary to a target sequence of the biological target; and
performing a second PCR process with a second set of molecules comprising dilution tag-associated primer regions complementary to nucleotide sequences of the different dilution tags.

18. The method of claim 15, wherein the abundance of the biological target is associated with a first time period, wherein the method further comprises determining a subsequent abundance of the biological target based on a subsequent modified dilution-tagged mixture and the relative concentration profile, wherein the subsequent abundance of the biological target is associated with a second time period, and wherein the abundance associated with the first time period and the abundance associated with the second time period facilitate characterization of a condition.

19. The method of claim 18, wherein the biological target is associated with a cancer, and wherein the abundance associated with the first time period and the abundance associated with the second time period facilitate characterization of a treatment response for the cancer.

20. The method of claim 15, wherein the different dilution tags are nucleic acids and determining the abundance of the biological target based on the modified dilution-tagged mixture and the relative concentration profile comprises:
determining sequence reads corresponding to the different dilution tags based on comparing nucleotide sequences of the sequence reads to nucleotide sequences of the different dilution tags, and
identifying a dilution tag combination, of the different dilution tags, with the greatest relative concentration while not being detected in the sequence reads; and
wherein determining the abundance of the biological target comprises determining the abundance based on a concentration indicated by the relative concentration profile for the identified dilution tag combination.

\* \* \* \* \*